(12) United States Patent
Southworth

(10) Patent No.: US 7,144,427 B2
(45) Date of Patent: Dec. 5, 2006

(54) APPARATUS AND METHOD FOR ADVANCING SYNOVIAL FLUID IN A PROSTHETIC JOINT

(75) Inventor: Carleton B. Southworth, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 223 days.

(21) Appl. No.: 10/310,288

(22) Filed: Dec. 5, 2002

(65) Prior Publication Data

US 2004/0111162 A1    Jun. 10, 2004

(51) Int. Cl.
*A61F 2/32* (2006.01)

(52) U.S. Cl. .................. 623/22.13; 623/23.68

(58) Field of Classification Search ............ 623/22.13, 623/22.14, 22.43, 22.45, 23.17, 23.41, 23.67, 623/23.68
See application file for complete search history.

(56) References Cited

U.S. PATENT DOCUMENTS

| | | | |
|---|---|---|---|
| 3,510,883 A | 5/1970 | Cathcart, III | |
| 3,512,184 A | 5/1970 | Grove | |
| 3,658,056 A * | 4/1972 | Huggler et al. | 623/22.43 |
| 3,683,421 A | 8/1972 | Martinie | |
| 4,032,994 A * | 7/1977 | Frey | 623/22.45 |
| 4,305,394 A | 12/1981 | Bertuch, Jr. | |
| 4,399,814 A | 8/1983 | Pratt, Jr. | |
| 4,467,637 A | 8/1984 | Rumberger | |
| 4,550,591 A | 11/1985 | Cox | |
| 4,702,236 A | 10/1987 | Tarabichy | |
| 4,714,478 A | 12/1987 | Fischer | |
| 4,731,088 A | 3/1988 | Collier | |
| 4,734,092 A | 3/1988 | Millerd | |
| 4,822,368 A | 4/1989 | Collier | |
| 4,840,631 A | 6/1989 | Mathys | |
| 4,851,006 A | 7/1989 | Tuke | |
| 4,936,855 A | 6/1990 | Sherman | |
| 5,039,698 A | 8/1991 | Leung | |
| 5,049,150 A | 9/1991 | Cozard | |
| 5,133,772 A | 7/1992 | Hack | |
| 5,152,794 A | 10/1992 | Davidson | |
| 5,294,030 A | 3/1994 | Jollivette | |
| 5,320,625 A | 6/1994 | Bertin | |
| 5,326,376 A | 7/1994 | Warner | |
| 5,358,525 A | 10/1994 | Fox | |
| 5,378,228 A * | 1/1995 | Schmalzried et al. | 604/8 |
| 5,379,754 A | 1/1995 | Tovey | |
| 5,389,107 A | 2/1995 | Nassar | |
| 5,413,606 A | 5/1995 | Fisk | |
| 5,458,653 A | 10/1995 | Davidson | |
| 5,511,563 A | 4/1996 | Diamond | |
| 5,514,182 A | 5/1996 | Shea | |
| 5,549,700 A | 8/1996 | Graham | |
| 5,554,111 A | 9/1996 | Morrey | |
| 5,556,429 A | 9/1996 | Felt | |

(Continued)

FOREIGN PATENT DOCUMENTS

DE    2 139 878    2/1973

(Continued)

*Primary Examiner*—Corrine McDermott
*Assistant Examiner*—Javier G. Bianco
(74) *Attorney, Agent, or Firm*—Barnes & Thornburg LLP

(57) ABSTRACT

A prosthetic orthopaedic head has a fluid chamber defined therein. A fluid filter is positioned in the fluid chamber. In response to a load being exerted on the prosthetic head, synovial fluid is advanced through a filter thereby removing debris from the synovial fluid. A method of operating a prosthesis is also disclosed.

10 Claims, 4 Drawing Sheets

U.S. PATENT DOCUMENTS

| | | | |
|---|---|---|---|
| 5,556,434 | A | 9/1996 | Epstein |
| 5,571,195 | A | 11/1996 | Johnson |
| 5,571,198 | A | 11/1996 | Drucker |
| 5,592,952 | A | 1/1997 | Bohn |
| 5,611,358 | A | 3/1997 | Suval |
| 5,641,323 | A | 6/1997 | Caldarise |
| 5,662,158 | A | 9/1997 | Caldarise |
| 5,665,118 | A | 9/1997 | LaSalle |
| 5,700,485 | A | 12/1997 | Berde |
| 5,701,912 | A | 12/1997 | Greening |
| 5,702,483 | A | 12/1997 | Kwong |
| 5,713,410 | A | 2/1998 | LaSalle |
| 5,734,959 | A | 3/1998 | Krebs |
| 5,752,526 | A | 5/1998 | Cosgrove |
| 5,755,807 | A | 5/1998 | Anstaett |
| 5,769,093 | A | 6/1998 | Bays |
| 5,770,559 | A | 6/1998 | Manning |
| 5,782,924 | A | 7/1998 | Johnson |
| 5,795,353 | A | 8/1998 | Felt |
| 5,807,303 | A * | 9/1998 | Bays .............................. 604/9 |
| 5,826,586 | A | 10/1998 | Mishra |
| 5,840,278 | A | 11/1998 | Coleman |
| 5,871,549 | A | 2/1999 | Jayashankar |
| 5,879,404 | A | 3/1999 | Bateman |
| 5,879,406 | A | 3/1999 | Lilley |
| 5,899,942 | A | 5/1999 | Berman |
| 5,904,720 | A | 5/1999 | Farrar |
| 5,916,270 | A | 6/1999 | Lipman |
| 5,925,077 | A | 7/1999 | Williamson |
| 5,926,685 | A | 7/1999 | Krebs |
| 5,954,694 | A | 9/1999 | Sunseri |
| 5,981,474 | A | 11/1999 | Manning |
| 5,997,582 | A | 12/1999 | Weiss |
| 6,010,711 | A | 1/2000 | O'Keefe |
| 6,051,014 | A | 4/2000 | Jang |
| 6,066,255 | A | 5/2000 | Anderson |
| 6,068,645 | A | 5/2000 | Tu |
| 6,096,084 | A | 8/2000 | Townley |
| 6,110,211 | A | 8/2000 | Weiss |
| 6,120,545 | A | 9/2000 | Hamelijnck |
| 6,122,797 | A | 9/2000 | Vanderlinden |
| 6,123,944 | A | 9/2000 | Chen |
| 6,132,470 | A | 10/2000 | Berman |
| 6,132,674 | A | 10/2000 | Compton |
| 6,143,035 | A | 11/2000 | McDowell |
| 6,187,050 | B1 | 2/2001 | Khalili |
| 6,209,621 | B1 | 4/2001 | Treacy |
| 6,248,131 | B1 | 6/2001 | Felt |
| 6,261,547 | B1 | 7/2001 | Bawa |
| 6,264,979 | B1 | 7/2001 | Svedman |
| 6,287,321 | B1 | 9/2001 | Jang |
| 6,306,175 | B1 | 10/2001 | Dearnaley |
| 6,315,647 | B1 | 11/2001 | Ghilardi |
| 6,350,341 | B1 | 2/2002 | Sunseri |
| 6,368,354 | B1 | 4/2002 | Burstein |
| 6,375,663 | B1 | 4/2002 | Ebner |
| 6,397,690 | B1 | 6/2002 | Schroder |
| 6,413,215 | B1 | 7/2002 | Wu |
| 6,432,141 | B1 | 8/2002 | Stocks |
| 6,692,529 | B1 * | 2/2004 | Shah .......................... 623/22.13 |
| 6,761,741 | B1 * | 7/2004 | Iesaka ....................... 623/22.26 |
| 2001/0018614 | A1 | 8/2001 | Bianchi |
| 2001/0053921 | A1 | 12/2001 | Jang |
| 2002/0049501 | A1 | 4/2002 | Storer |
| 2002/0052659 | A1 | 5/2002 | Hayes |
| 2002/0065562 | A1 | 5/2002 | Storer |
| 2002/0143402 | A1 | 10/2002 | Steinberg |
| 2003/0060891 | A1 | 3/2003 | Shah |

FOREIGN PATENT DOCUMENTS

| | | |
|---|---|---|
| DE | 27 42 464 | 3/1979 |
| DE | 100 37 504 | 2/2002 |
| EP | 0346294 A1 | 12/1989 |
| EP | 0179084 B1 | 6/1991 |
| EP | 0523926 A2 | 1/1993 |
| EP | 0640323 A1 | 3/1995 |
| EP | 0739613 A1 | 10/1996 |
| EP | 0803234 A1 | 10/1997 |
| EP | 0741552 B1 | 11/1997 |
| EP | 0611558 B1 | 5/1999 |
| EP | 0927546 A2 | 7/1999 |
| EP | 1023872 A2 | 8/2000 |
| EP | 0668062 B1 | 8/2001 |
| EP | 1138283 A2 | 10/2001 |
| EP | 1138284 A1 | 10/2001 |
| EP | 0755232 B1 | 11/2001 |
| EP | 0748193 B1 | 12/2001 |
| EP | 0830114 B1 | 8/2002 |
| EP | 0841041 B1 | 9/2002 |
| WO | WO92/09886 A1 | 6/1992 |
| WO | WO92/19233 A2 | 11/1992 |
| WO | WO93/11721 A1 | 6/1993 |
| WO | WO94/08599 A1 | 4/1994 |
| WO | WO95/20369 A1 | 8/1995 |
| WO | WO95/23566 A1 | 9/1995 |
| WO | WO95/30388 A1 | 11/1995 |
| WO | WO95/34331 A1 | 12/1995 |
| WO | WO96/18357 A2 | 6/1996 |
| WO | WO96/25127 A1 | 8/1996 |
| WO | WO96/29030 A1 | 9/1996 |
| WO | WO97/23166 A1 | 7/1997 |
| WO | WO98/14140 A1 | 4/1998 |
| WO | WO98/55050 A1 | 12/1998 |
| WO | WO99/15113 A1 | 4/1999 |
| WO | WO99/47137 A1 | 9/1999 |
| WO | WO99/56674 A1 | 11/1999 |
| WO | WO00/01324 A1 | 1/2000 |
| WO | WO00/21604 A1 | 4/2000 |
| WO | WO00/28925 A2 | 5/2000 |
| WO | WO00/47214 A1 | 8/2000 |
| WO | WO00/57820 A1 | 10/2000 |
| WO | WO01/37734 A1 | 5/2001 |
| WO | WO01/74470 A1 | 10/2001 |
| WO | WO01/76483 A2 | 10/2001 |
| WO | WO02/07652 A1 | 1/2002 |
| WO | WO02/13730 A2 | 2/2002 |
| WO | WO02/43626 A1 | 6/2002 |

* cited by examiner

APPARATUS AND METHOD FOR ADVANCING SYNOVIAL FLUID IN A PROSTHETIC JOINT

FIELD OF THE DISCLOSURE

The present disclosure relates generally to orthopaedic prostheses and methods of operating the same.

BACKGROUND

During the lifetime of a patient, it may be necessary to perform a joint replacement procedure on the patient as a result of, for example, disease or trauma. The joint replacement procedure may involve the use of a prosthesis which is implanted into one of the patient's bones. In the case of a hip replacement procedure, a femoral prosthesis is implanted into the patient's femur. The femoral prosthesis typically includes an elongated stem component which is implanted into the intramedullary canal of the patient's femur and a spherically-shaped head which bears against the patient's acetabulum or a prosthetic replacement acetabular cup. Subsequent to performance of a joint replacement procedure, a patient is typically monitored for the onset of any issues such as osteolysis, articular bearing surface wear, infection, aseptic loosening, and subsidence.

SUMMARY

According to one aspect of the present disclosure, there is provided a prosthetic head component. The head component, in essence, functions as a pump or part thereof which, in response to a load being exerted thereon, advances synovial fluid through a filter. The filter is positioned and configured to filter the synovial fluid. It is contemplated that the filter may illustratively be positioned in the head component. In such a way, debris is removed from the synovial fluid. Moreover, the synovial fluid exiting the prosthetic head component may be directed onto the articulating surface of the head component, along with the surface on which it bears, thereby lubricating the joint.

Such a prosthetic head component may be constructed of a flexible material such as a flexible metallic material. It may include a synovial fluid inlet valve and a synovial fluid outlet valve.

The filter may illustratively be positioned in an elongated bore defined in a stem component coupled to the head component.

A method of operating a prosthesis is also disclosed. The method includes the step of advancing synovial fluid through the head component of the prosthesis in response to the exertion of a load on the prosthesis. A filter is positioned in the fluid path thereby filtering the synovial fluid as it is advanced through the prosthetic head component.

The method may illustratively include advancing synovial fluid through an inlet valve subsequent to advancement through the fluid filter. In some cases, the head component will be pre-charged or pre-loaded with a treatment material selected from the group consisting of saline, an antibiotic fluid, a joint lubricant, an analgesic, or some combination of thereof.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
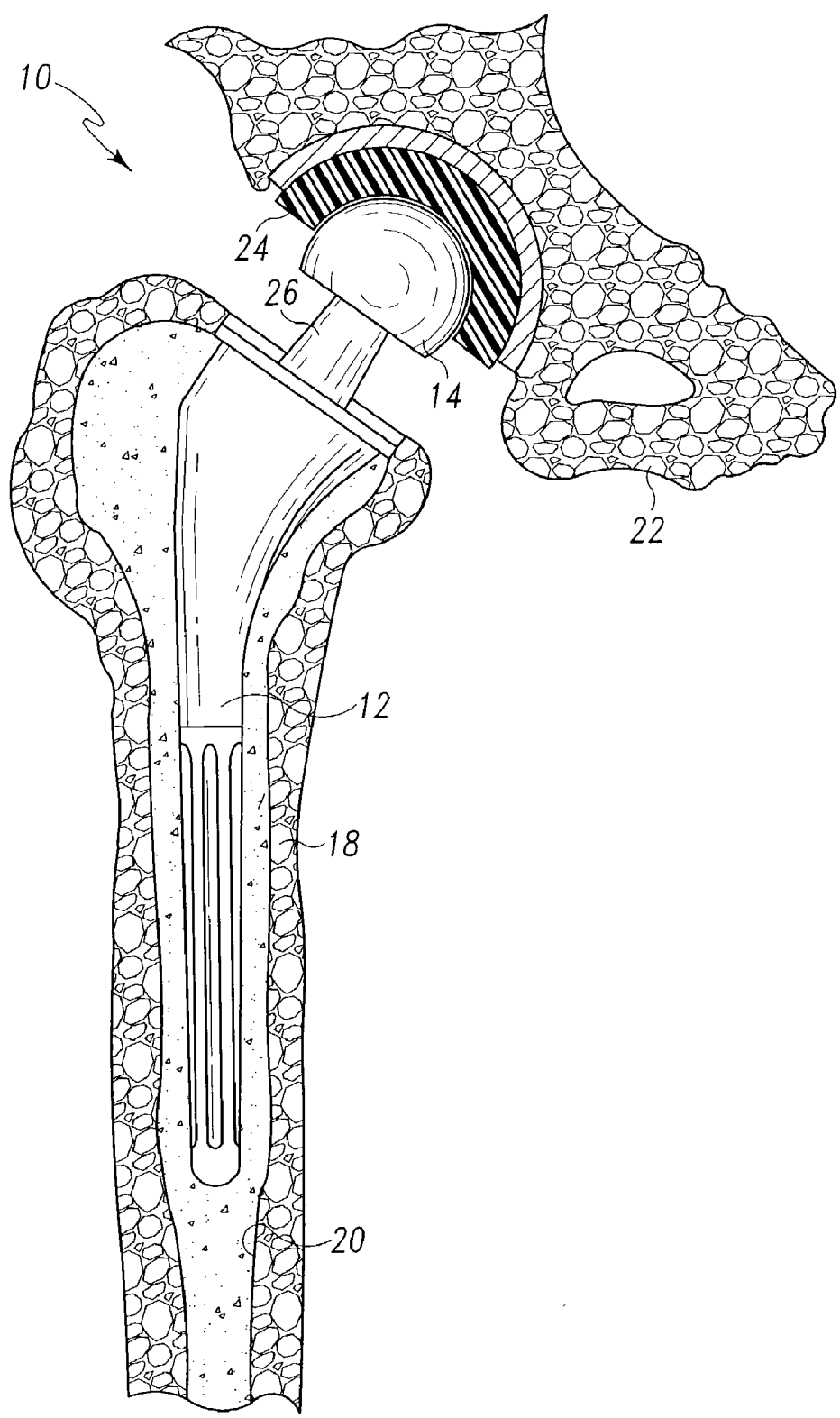
FIG. 1 is a partial cross sectional view of an implanted hip prosthesis.

Referring now to FIG. 1, there is shown an implantable prosthesis 10 for use during performance of a joint replacement procedure such as a hip replacement procedure. It should be appreciated that although the concepts of the present disclosure are herein exemplarily described in regard to a prosthesis for use in the performance of a hip replacement procedure, the concepts of the present disclosure may be utilized in regard to a prosthesis for use in replacement procedures at numerous other joint locations throughout the body. For example, the concepts of the present disclosure may be utilized in the construction of a prosthesis for use in the performance of a shoulder, knee, wrist, or ankle procedure.

The femoral prosthesis 10 includes a stem component 12 and a generally-spherically shaped head component 14. The prosthesis 10 is configured to be implanted into a femur 18 of a patient in order to replace certain natural features of the patient's femur 18 as a result of, for example, disease or trauma. The prosthesis 10 is implanted into a surgically prepared (e.g. reamed and/or broached) intramedullary canal 20 of the femur 18. The modular prosthesis 10 may be press fit into the intramedullary canal 20, or alternatively, may be secured within the intramedullary canal 20 by the use of bone cement.

In such a manner, the prosthesis 10 may be utilized to secure the patient's femur 18 for movement relative to the patient's pelvis 22. In particular, the head component 14 is positioned to bear on either the patient's natural acetabulum or a prosthetic socket in the form of a prosthetic cup 24 which has been implanted into the patient's pelvis 22 to replace his or her acetabulum. In such a manner, the prosthesis 10 and the natural or artificial acetabulum collectively function as a system which replaces the natural "ball and socket" joint of the patient's hip.

The stem component 12 may be embodied in a number of different configurations in order to fit the needs of a given patient's anatomy and provide a variety of fixation options (e.g. textures and geometries) and sizes. In particular, the stem component 12 may be configured in various different lengths in order to conform to the patient's anatomy (e.g. a relatively long stem component 12 for use with a long femur 18, a relatively short stem for use with a short femur 18, etcetera). Moreover, the stem component 12 may also be embodied in a bow-shaped configuration if required by a given patient's anatomy. Yet further, the stem component 12 may also be embodied in various diameters and outer textures if required by a given patient's anatomy.

The stem component 12 includes a trunnion 26 extending outwardly from the body thereof. As shown in FIG. 1, the head component 14 is taper fit or otherwise secured to the trunnion 26.

Figure 2:
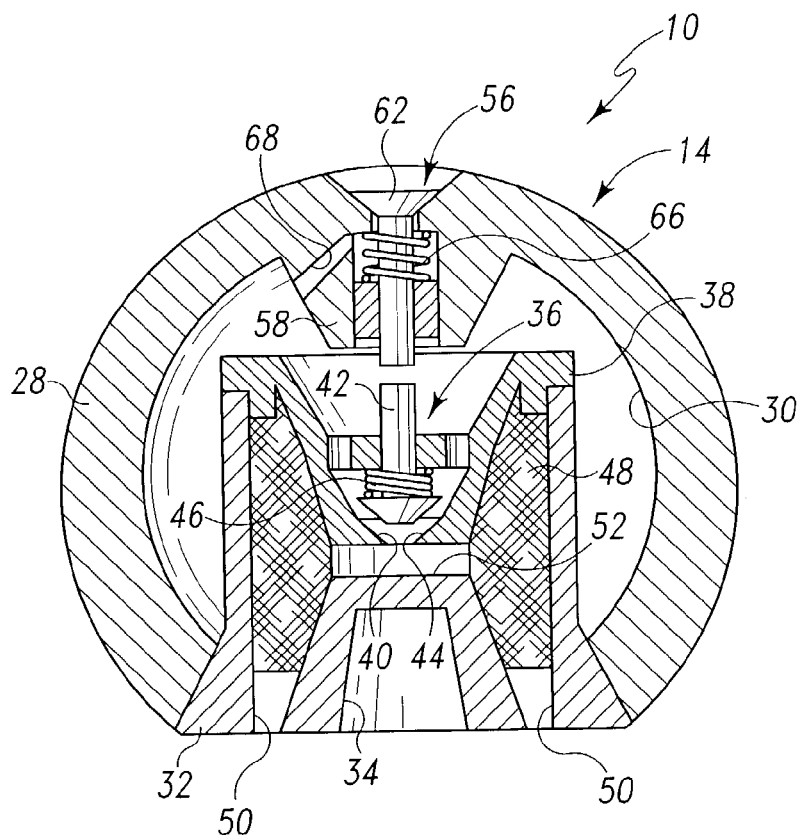
FIGS. 2 and 3 are enlarged cross sectional views of the head component of the hip prosthesis of FIG. 1, note that the valve members and the spring are not shown in cross section for clarity of description.
Figure 3:
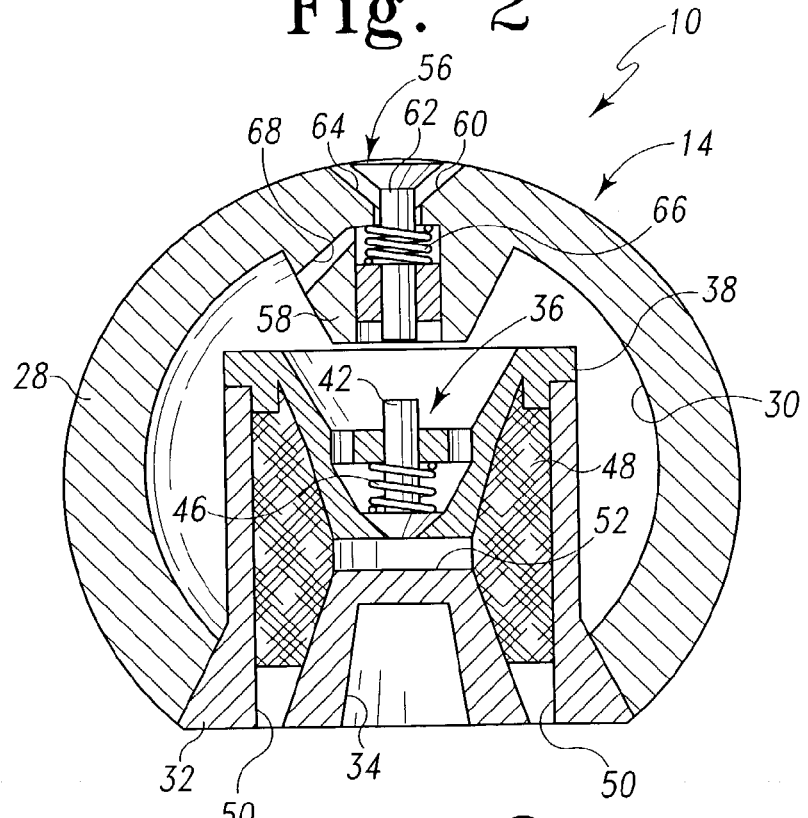

Referring now to FIGS. 2 and 3, there is shown the head component 14 in greater detail. The head component 14 has a generally spherical-shaped hollow body 28 which defines a fluid chamber 30. The body 28 is illustratively constructed of a material which allows the hollow body 28 to flex, compress, or otherwise deform slightly under load such as, for example, the load exerted on the head component 14 when the patient walks. Such flexing of the body 28 reduces the volume of the fluid chamber 30 thereby increasing fluid pressure therein. When the load is removed from the head component 14, the volume returns to its pre-load state. As will be described herein in greater detail, such changes in volume of the fluid chamber 30 allows the head component 14 to function, in essence, as a synovial fluid pump.

A filter housing 32 is taper fit or otherwise secured to the body 28. The filter housing 32 has defined therein a tapered bore 34 into which the trunnion 26 of the stem component 12 is secured.

The head component 14 also includes a synovial fluid inlet valve 36. In particular, a valve housing 38 is secured to the filter housing 32. The valve housing 38 has defined therein a valve seat 40. An inlet valve member 42 is movable into and out of contact with the valve seat 40 so as to selectively block a flow of synovial fluid through a fluid opening 44. As shown in FIG. 3, a spring 46 biases the inlet valve 36 into its closed position. In particular, the spring 46 biases the valve member 42 into sealing engagement with the valve seat 40.

Although the inlet valve 36 is herein described as a spring-biased bevel valve, it should be appreciated that the inlet valve 36 may be embodied as any type of valve such as, for example, a Hakim Programmable Hydrocepualus Valve utilizing a ruby ball and a sapphire seat. Moreover, it should also be appreciated that any number and size of inlet valves 36 may be utilized in the construction of the head component 14.

A fluid filter 48 is positioned in the filter housing 32 at a position fluidly interposed between a number of synovial fluid inlets 50 and the synovial fluid inlet valve 36. Hence, synovial fluid is advanced into the filter housing 32 via the fluid inlets 50, through the fluid filter 48, and into an annular chamber 52. Upon opening of the synovial fluid inlet valve 36, synovial fluid is advanced out of the annular chamber 52, through the fluid opening 44 and into the fluid chamber 30. In such a way, synovial fluid entering the fluid chamber 30 is filtered prior to introduction to the inlet valve 36 thereby reducing the occurrences of debris clogging the inlet valve 36.

The head component 14 also includes a synovial fluid outlet valve 56. In particular, the body 28 of the head component 14 has defined therein a valve seat 60. An outlet valve member 62 is movable into and out of contact with the valve seat 60 so as to selectively block a flow of synovial fluid through a fluid outlet 64 and out of the fluid chamber 30. As shown in FIG. 2, a spring 66 biases the outlet valve 56 into its closed position. In particular, the spring 66 biases the valve member 62 into sealing engagement with the valve seat 60.

The body 28 of the head component 14 also has defined therein a valve housing 58. The spring 66 and the stem of the valve member 62 are housed in the valve housing 58. Moreover, a fluid passage 68 is defined in the valve housing 58 so as to fluidly couple the fluid chamber 30 and the fluid outlet 64. In such a way, when fluid pressure within the fluid chamber 30 exceeds the bias of the spring 66, the outlet valve 56 is opened (i.e., the valve member 62 is spaced apart from its valve seat 60) thereby expelling synovial fluid out of the fluid chamber 30, through the fluid passage 68, and out of the fluid outlet 64.

As with the inlet valve 36, although the outlet valve 56 is herein described as a spring-biased bevel valve, it should be appreciated that the outlet valve 56 may be embodied as any type of valve such as, for example, a Hakim Programmable Hydrocepualus Valve utilizing a ruby ball and a sapphire seat. Moreover, it should also be appreciated that any number and size of outlet valves 56 may be utilized in the construction of the head component 14. Even further, in certain embodiments of the head component 14, a number of fluid outlet pores in lieu of the outlet valve 56 may be used to "expel" the synovial fluid.

As alluded to above, the aforedescribed configuration of the head component 14 allows for the in-vivo pumping and filtering of synovial fluid. In particular, as load is exerted on and removed from the head component 14, as will happen during loading and unloading cycles associated with walking, the body 28 of the head component 14 is flexed and then subsequently relaxed thereby pumping synovial fluid through the fluid chamber 30 and hence the fluid filter 48. More specifically, the illustrative hollow head body 28 flexes, compresses, or otherwise deforms slightly under load. Such a change in shape reduces the internal volume of the fluid chamber 30 of the head component 14 thereby increasing fluid pressure therein. Such an increase in fluid pressure causes the outlet valve 56 to open thereby ejecting synovial fluid through the fluid outlet 64. As more specifically discussed hereinafter, while the illustrative head body 28 flexes to provide the desired pumping action, other relative movement in the prosthesis 10 may be used to accomplish pumping action.

As load is removed from the head component 14, the body 28 of the head component 14 returns its pre-load shape (e.g., to a more nearly spherical shape) thereby decreasing fluid pressure in the fluid chamber 30. As such, the inlet valve 36 is opened thereby drawing synovial fluid through the fluid inlets 50, through the filter 48, through the fluid opening 44, and into the fluid chamber 30. Synovial fluid drawn into the fluid chamber 30 will be expelled during subsequent load cycles.

It should be appreciated that prior to implantation, the fluid chamber 30 of the head component 14 may be pre-loaded with saline, an antibiotic fluid, a joint lubricant such as Arthrease™, an analgesic, or some combination of thereof. As a result, in addition to the filtering of synovial fluid, the head component 14 may also be operated to reduce the occurrences of infection, pain, and wear. In a similar manner as the prosthesis described herein in regard to FIGS. 4 and 5, a port for "recharging" the fluid chamber 30 of the head component 14 with antibiotics or other fluids in-vivo may also be included. In other words, the head component 14 may be used as a drug delivery system.

Figure 4:
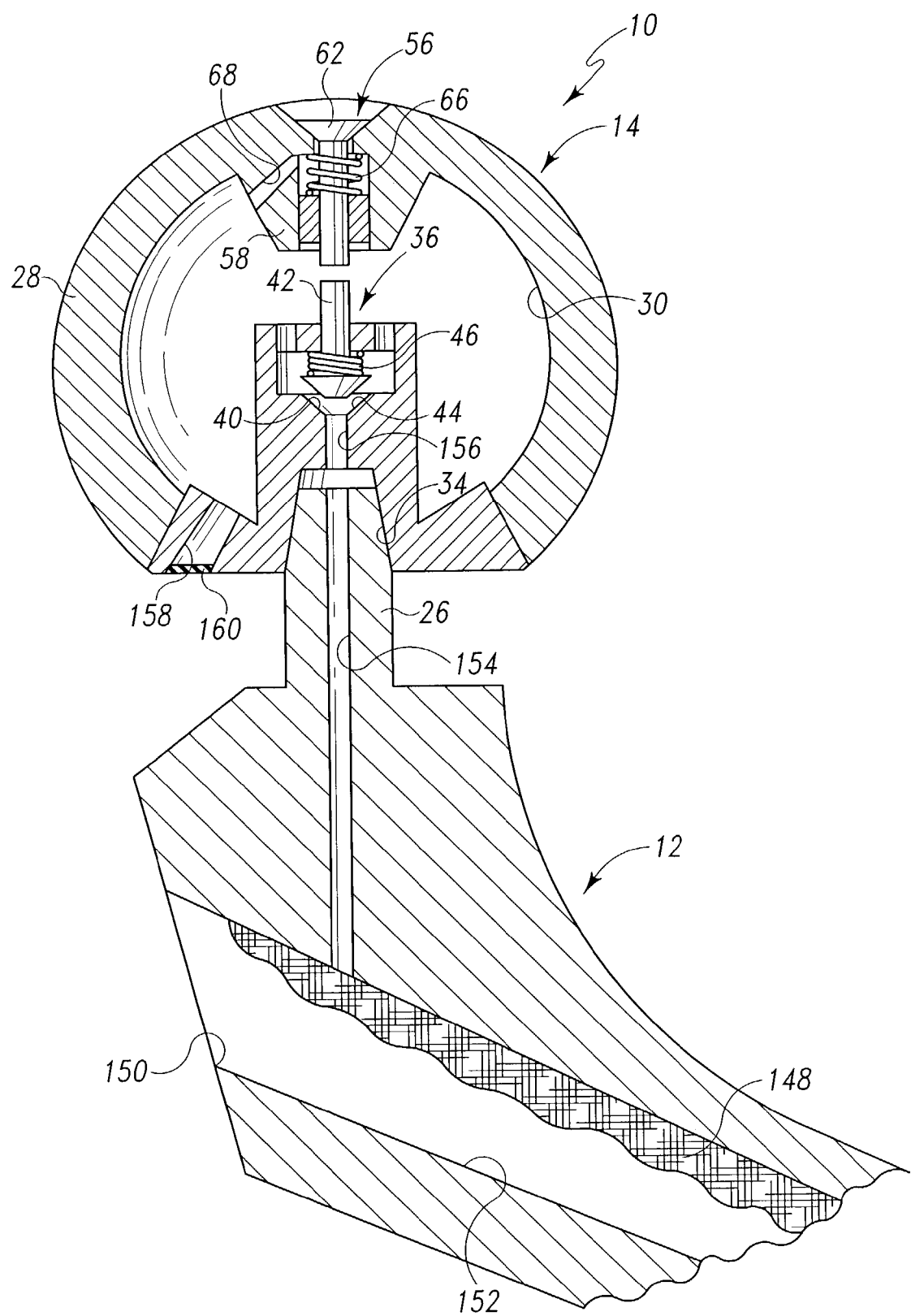
FIGS. 4 and 5 are enlarged cross sectional views of another embodiment of the hip prosthesis of FIG. 1, note that the valve members and their associate springs are not shown in cross section for clarity of description.
Figure 5:
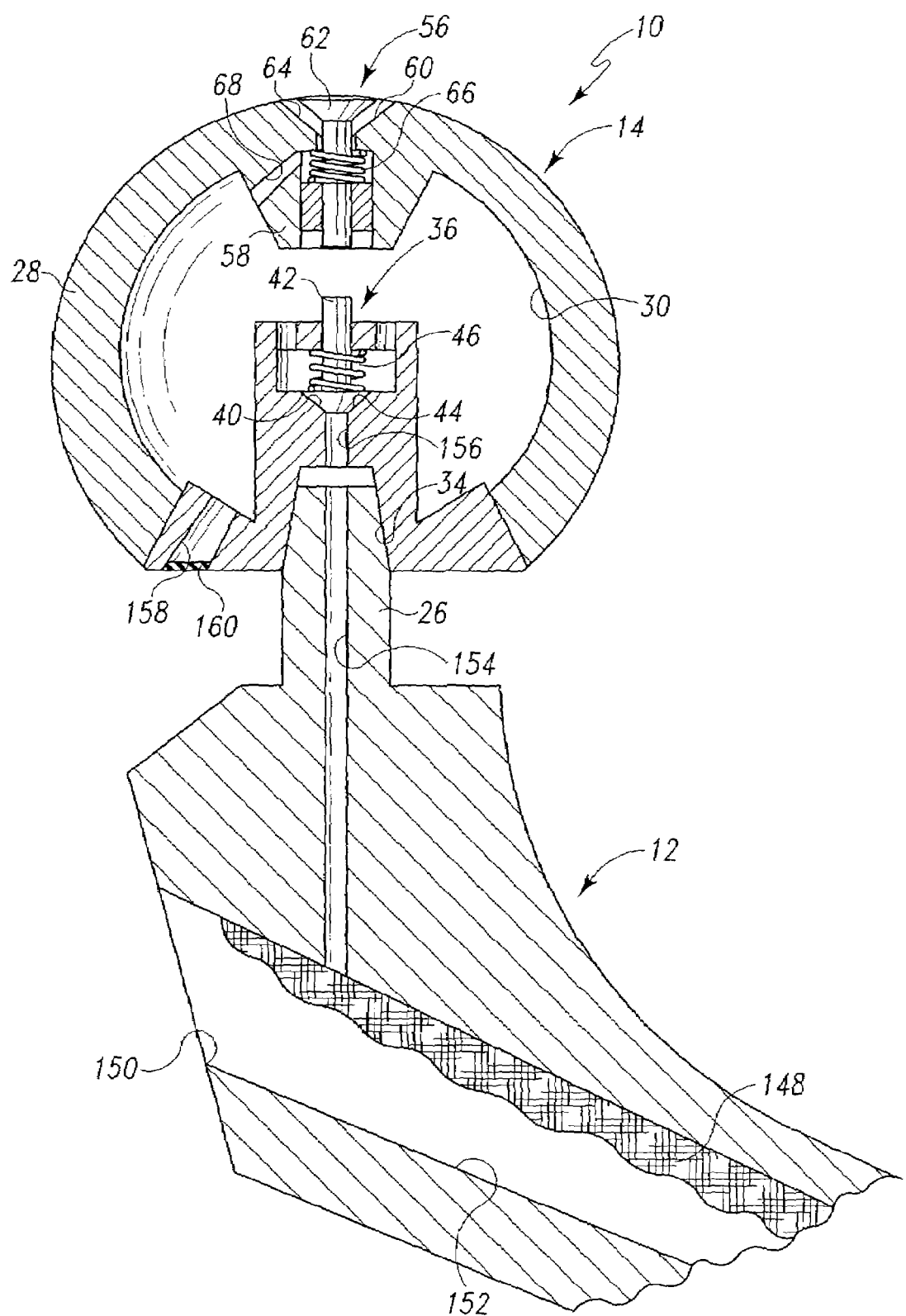

Referring now to FIGS. 4 and 5, there is shown another embodiment of the hip prosthesis 10 which is similar to the embodiment shown in FIGS. 2 and 3. The same reference numerals are used in FIGS. 4 and 5 to designate common components which were previously discussed in regard to FIGS. 2 and 3 with additional discussion thereof being unwarranted. The prosthesis of FIGS. 4 and 5 is essentially the same as the prosthesis of FIGS. 2 and 3 with the exception that the synovial fluid inlet(s) 150 of the prosthesis are defined in the stem component 12 as opposed to the head component 14. The fluid filter 148 is likewise positioned in the stem component 12. Such a configuration allows for the filtering and trapping of relatively large amounts of debris.

In the exemplary embodiment shown in FIGS. 4 and 5, an elongated bore 152 is defined in the stem component 12. The synovial fluid inlet(s) 150 define one end of the elongated bore 152. A fluid passage 154 extends from the bore 152 through the body and the trunnion 26 of the stem component 12 so as to fluidly couple the bore 152 (and hence the fluid inlet 150) to a fluid inlet passage 156 defined in the valve housing 132 of the head component 14. In such a way, synovial fluid entering the fluid inlet(s) 150 may be advanced through the fluid filter 148 and into the fluid chamber 30 of the head component 14 when the inlet valve 36 is opened via a fluid path which includes the elongated bore 152, the fluid passage 154 of the stem component 12, and the fluid inlet passage 156 of the valve housing 132.

Similar to the configuration of the prosthesis of FIGS. 2 and 3, the aforedescribed configuration of the prosthesis of FIGS. 4 and 5 allows for the in-vivo pumping and filtering of synovial fluid. In particular, as load is exerted on and removed from the head component 14, as will happen during loading and unloading cycles associated with walking, the body 28 of the head component 14 is flexed and then subsequently relaxed thereby pumping synovial fluid through the fluid chamber 30 and hence the fluid filter 148. More specifically, the hollow head body 28 flexes, compresses, or otherwise deforms slightly under load. Such a change in shape reduces the internal volume of the fluid chamber 30 of the head component 14 thereby increasing fluid pressure therein. Such an increase in fluid pressure causes the outlet valve 56 to open thereby ejecting synovial fluid through the fluid outlet 64.

As load is removed from the head component 14, the body 28 of the head component 14 returns its pre-load shape (e.g., to a more nearly spherical shape) thereby decreasing fluid pressure in the fluid chamber 30. As such, the inlet valve 36 is opened thereby drawing synovial fluid through the fluid inlet(s) 150 and into the bore 152 of the stem component 12, through the filter 148, through the fluid passage 154 of the stem component 12, through the inlet passage 156 of the head component, and into the fluid chamber 30. Synovial fluid drawn into the fluid chamber 30 will be expelled during subsequent load cycles.

As with the head component 14 of FIGS. 2 and 3, the fluid chamber 30 of the head component 14 of FIGS. 4 and 5 may be pre-loaded with saline, an antibiotic fluid, a joint lubricant such as Arthrease™, an analgesic, or some combination thereof. As a result, in addition to the filtering of synovial fluid, the head component 14 may also be operated to reduce the occurrences of infection, pain, and wear.

Moreover, the head component 14 of FIGS. 4 and 5 has a port 158 for "recharging" the fluid chamber 30 of the head component 14 with antibiotics or other fluids in-vivo. The recharging port 158 may be sealed with a self-sealing silicone seal 160 in order to prevent the unwanted introduction of debris or liquids into the fluid chamber 30 through the port 158.

As described herein, the concepts of the present disclosure have a number of advantages. For example, the concepts of the present disclosure provide for in-vivo filtering of debris from synovial fluid. Moreover, the concepts of the present disclosure provide for in-vivo lubrication of a joint. In addition, the head components of the present disclosure may be pre-loaded with antibiotic, joint lubricant such as Arthrease™, or an analgesic, or a combination of these. Hence, the concepts of the present disclosure provide for the construction of a prosthesis that removes wear debris and reduces osteolysis, reduces third body wear, lubricates the articular surfaces of the joint, and reduces the probability of infection. Moreover, the prosthetic head components described herein, such as the head component 14 of FIGS. 2 and 3, may be used in the performance of a minimally invasive surgical procedure to salvage natural femoral or acetabular components showing early signs of osteolysis.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

For example, as described herein, although the concepts of the present disclosure have been exemplary described in regard to the construction of a humeral head of a hip prosthesis, it should be appreciated that the concepts of the present disclosure may be utilized in the construction of other types of prosthetic "heads." For example, the concepts of the present disclosure may be utilized in the construction of a head of a knee prosthesis, a shoulder prosthesis, an ankle prosthesis, or a wrist prosthesis. Moreover, the concepts of the present disclosure may be utilized in the construction of any hollow cavity within an orthopaedic prosthesis that may flex, compress, or otherwise deform under load. In other words, the concepts of the present disclosure are not limited to use only in the construction of prosthetic heads.

Further, although it is described herein that the head component decreases in volume under load and ejects fluid under load, the opposite situation where load increases the interior volume and draws fluid in and unloading ejects fluid is also contemplated. For example, exerting force on the top point of a slightly oval shaped body will increase the interior volume as the body distorts to a more nearly spherically-shaped form. This would draw fluid in into the chamber when load is exerted on the body, and fluid would be ejected from the chamber as load is removed and the body returns to its original, slightly oval shape.

Moreover, the pump action for advancing synovial fluid may be provided by relative movement other than or in addition to flexure of the body of the head component. For example, the head component may be mounted on the stem component in a manner to allow for controlled and resisted movement between the two components thereby proving pumping action. The concept, therefore, is to provide for controlled amounts of resisted or resilient movement by the normal loads placed on the prosthesis. Such movement will change the volume of the chamber (e.g., reduce the volume of the chamber) under load and change the volume of the chamber again (e.g., increase the volume of the chamber) when the load is removed.

The invention claimed is:

1. An orthopaedic prosthesis, comprising:
    a head component having defined therein (i) a chamber and (ii) a fluid outlet in communication with the chamber,
    a synovial fluid inlet valve positioned in the chamber,
    a synovial fluid inlet, and
    a fluid filter fluidly interposed between the synovial fluid inlet and the synovial fluid inlet valve.

2. The prosthesis of claim 1, wherein the head component is constructed of a flexible material.

3. The prosthesis of claim 1, wherein the head component is constructed of a flexible metallic material.

4. The prosthesis of claim 1, further comprising a synovial fluid outlet valve positioned in the chamber.

5. The prosthesis of claim 4, wherein:
    the synovial fluid inlet valve is positionable in an open valve position and a closed valve position,
    the synovial fluid outlet valve is positionable in an open valve position and a closed valve position,
    the head component is positionable in a flexed orientation and an unflexed orientation,
    when the head component is positioned in the flexed orientation, (i) the synovial fluid inlet valve is positioned in its closed valve position, and (ii) the synovial fluid outlet valve is positioned in its open valve position, and
    when the head component is positioned in the unflexed orientation, (i) the synovial fluid inlet valve is positioned in its open valve position, and (ii) the synovial fluid outlet valve is positioned in its closed valve position.

6. The prosthesis of claim 4, wherein:
    the synovial fluid inlet valve is positionable in an open valve position and a closed valve position,
    the synovial fluid outlet valve is positionable in an open valve position and a closed valve position,
    when a load is exerted on the head component, (i) the synovial fluid inlet valve is positioned in its closed valve position, and (ii) the synovial fluid outlet valve is positioned in its open valve position, and
    when the load is removed from the head component, (i) the synovial fluid inlet valve is positioned in its open valve position, and (ii) the synovial fluid outlet valve is positioned in its closed valve position.

7. The prosthesis of claim 1, wherein:
    the synovial fluid inlet valve is positionable in an open valve position and a closed valve position,
    the head component is positionable in a flexed orientation and an unflexed orientation,
    the synovial fluid inlet valve is positioned in its closed valve position when the head component is positioned in the flexed orientation, and
    the synovial fluid inlet valve is positioned in its open valve position when the head component is positioned in the unflexed orientation.

8. The prosthesis of claim 1, wherein:
    the synovial fluid inlet valve is positionable in an open valve position and a closed valve position,
    the synovial fluid inlet valve is positioned in its closed valve position when a load is exerted on the head component, and
    the synovial fluid inlet valve is positioned in its open valve position when the load is removed from the head component.

9. A prosthetic head component, comprising:
    a body defining a fluid chamber,
    a fluid filter positioned in the fluid chamber,
    a fluid inlet valve positioned in the fluid chamber at a location downstream of the fluid filter, and
    a fluid outlet valve positioned in the fluid chamber.

10. The prosthetic head component of claim 9, further comprising a fluid outlet defined in the body.

* * * * *